United States Patent [19]

Braig et al.

[11] Patent Number: 5,615,672
[45] Date of Patent: Apr. 1, 1997

[54] SELF-EMISSION NONINVASIVE INFRARED SPECTROPHOTOMETER WITH BODY TEMPERATURE COMPENSATION

[75] Inventors: James R. Braig, Alameda, Calif.;
Daniel S. Goldberger, Boulder, Colo.;
Bernhard B. Sterling, Danville, Calif.

[73] Assignee: Optiscan, Inc., Alameda, Calif.

[21] Appl. No.: 353,099

[22] Filed: Dec. 9, 1994

Related U.S. Application Data

[63] Continuation-in-part of Ser. No. 247,311, May 23, 1994, Pat. No. 5,515,847, which is a continuation-in-part of Ser. No. 10,634, Jan. 28, 1993, Pat. No. 5,313,941.

[51] Int. Cl.$^6$ ........................................................... A61B 5/00
[52] U.S. Cl. ................................................. 128/633; 128/664
[58] Field of Search ..................................... 128/633, 664

[56] References Cited

U.S. PATENT DOCUMENTS

| | | | |
|---|---|---|---|
| 3,958,560 | 5/1976 | March | 128/2 A |
| 4,655,225 | 4/1987 | Dahne et al. | 128/633 |
| 5,009,230 | 4/1991 | Hutchinson | 128/633 |
| 5,028,787 | 7/1991 | Rosenthal et al. | 250/341 |
| 5,036,462 | 7/1991 | Kaufman et al. | 364/413.01 |
| 5,040,539 | 8/1991 | Schmitt et al. | 128/633 |
| 5,070,874 | 12/1991 | Barnes et al. | 128/633 |
| 5,137,023 | 8/1992 | Mendelson et al. | 128/633 |
| 5,140,985 | 8/1992 | Schroeder et al. | 128/632 |
| 5,159,936 | 11/1992 | Yelderman | 128/736 |
| 5,190,039 | 3/1993 | Takeuchi et al. | 128/633 |
| 5,313,941 | 5/1994 | Braig et al. | 128/633 |
| 5,337,745 | 8/1994 | Benaron | 128/633 |
| 5,379,764 | 1/1995 | Barnes et al. | 128/633 |

FOREIGN PATENT DOCUMENTS

| | | |
|---|---|---|
| 612271 | 7/1979 | Switzerland . |
| WO91/15992 | 10/1991 | WIPO . |
| WO93/00855 | 1/1993 | WIPO . |

*Primary Examiner*—Angela D. Sykes
*Assistant Examiner*—Eric F. Winakur
*Attorney, Agent, or Firm*—Woodcock Washburn Kurtz Mackiewicz & Norris

[57] ABSTRACT

A method and apparatus for monitoring glucose, ethyl alcohol and other blood constituents in a noninvasive manner. The measurements are made by monitoring infrared absorption of the desired blood constituent in the long infrared wavelength range where the blood constituent has a strong and distinguishable absorption spectrum. The long wavelength infrared energy emitted by the person as heat is monitored and the infrared absorption of particular constituents in the blood (such as glucose or blood alcohol) is measured at characteristic infrared absorption wavelengths for those constituents. The measurements are preferably synchronized with systole and diastole of the cardiac cycle so that the signal contribution caused by veins and tissues (which do not pulse) may be cancelled when a ratio of the detected signals is taken. On the other hand, if no synchronization is provided, the spectrophotometer may measure the arterial, venous and tissue constituent concentrations simultaneously, which may be desired in some circumstances. The internal "blackbody" energy level of an infrared emissions source such as a vascularized appendage prior to glucose absorption is measured and used to compensate temperature dependent effects in the concentration calculation. The internal energy level is then ratioed to the actual measured energy and used to compute the percentage of energy absorbed by the glucose. Discontinuities in the ratio are eliminated by converting the absorption measurements from voltages to watts.

29 Claims, 4 Drawing Sheets

SELF-EMISSION NONINVASIVE INFRARED SPECTROPHOTOMETER WITH BODY TEMPERATURE COMPENSATION

CROSS-REFERENCE TO RELATED APPLICATIONS

This application is a continuation-in-part application of U.S. patent application Ser. No. 08/247,311, filed May 23, 1994, now U.S. Pat. No. 5,515,847 which is, in turn, a continuation-in-part application of U.S. patent application Ser. No. 08/010,634, filed Jan. 28, 1993, now U.S. Pat. No. 5,313,941.

BACKGROUND OF THE INVENTION

1. Field of the Invention

The present invention relates to an instrument and a method for noninvasively measuring the concentration of glucose, dissolved carbon dioxide, ethyl alcohol or other constituents in a person's blood. In particular, the present invention relates to an instrument and associated method for monitoring the infrared absorption of such constituents in a person's blood at long infrared wavelengths where such constituents have strong and distinguishable absorption spectra by measuring specific absorptions of the constituents of interest within the infrared energy band emitted from the person's body.

BRIEF DESCRIPTION OF THE PRIOR ART

According to the American Diabetes Association, more than 14 million people in the United States have diabetes, though about half of them are not aware of it. Almost 750,000 people per year are diagnosed with diabetes, while approximately 150,000 die from the disease or its complications each year. Since people with diabetes are at risk for blindness, kidney disease, heart disease and stroke, they need to control the disease by closely monitoring their blood glucose levels and carefully controlling the intake of insulin and glucose. Numerous home diagnostic devices have been developed for this purpose.

Spectroscopic glucose monitoring techniques using infrared light are known in the prior art and are the subject of the present application. Prior art spectroscopic techniques provide non-invasive solutions to the problem of measuring glucose in the bloodstream. According to one technique, near infrared spectroscopy, light is passed through a finger or suitable appendage for measuring glucose levels in vivo. Unfortunately, this technique suffers from two sources of inaccuracy: tissue interference and lack of specificity. Moreover, while the near infrared wavelengths used are easily and economically generated by light emitting diodes (LEDs) and solid state lasers, they are not in a range specifically absorbed by glucose. This lack of "fingerprint" absorbance and interference from tissue pigment and condition render the technique useless for accurate concentration determination but possibly acceptable for trending if stability can be maintained. Samples of prior art patents describing such spectroscopic techniques are described below.

Kaiser describes in Swiss Patent No. 612,271 a technique in which an infrared laser is used as the radiation source for measuring glucose concentration in a measuring cell. The measuring cell consists of an ATR measuring prism which is wetted by the person's blood and an ATR reference prism which is wetted with a comparison solution. $CO_2$ laser radiation is led through the measuring cell and gathered before striking a signal processing device. A chopper placed before the measuring cell allows two voltages to be obtained corresponding to the signal from the sample and the reference prisms. Due to absorption corresponding to the concentration of the substance measured in the blood, the difference between the resulting voltages is proportional to the concentration. Unfortunately, the infrared laser used by Kaiser has the undesirable side-effect of heating the blood, which may be harmful to the person, and also does not overcome the effects of tissue absorption. Although Kaiser suggests that heating of the blood may be prevented by using extra-corporeal cuvettes of venous blood and high blood flow rates, Kaiser does not describe a noninvasive technique for measuring glucose concentration which overcomes the effects of tissue absorption or other sources of error which are present in the portion of the infrared spectrum were Kaiser makes his measurements.

March in U.S. Pat. No. 3,958,560 describes a "noninvasive" automatic glucose sensor system which senses the rotation of polarized infrared light which has passed through the cornea of the eye. March's glucose sensor fits over the eyeball between the eyelid and the cornea and measures glucose as a function of the amount of radiation detected at the detector on one side of the person's cornea. Unfortunately, while such a technique does not require the withdrawal of blood and is thus "noninvasive", the sensor may cause considerable discomfort to the person because of the need to place it on the person's eye. A more accurate and less intrusive system is desired.

Hutchinson describes in U.S. Pat. No. 5,009,230 a personal glucose monitor which also uses polarized infrared light to noninvasively detect glucose concentrations in the person's bloodstream. The amount of rotation imparted on the polarized light beam is measured as it passes through a vascularized portion of the body for measuring the glucose concentration in that portion of the body. Although the monitor described by Hutchinson need not be mounted on the person's eye, the accuracy of the measurement is limited by the relatively minimal absorption of glucose in the 940–1000 nm range used by Hutchinson.

Dahne et al. in U.S. Pat. No. 4,655,225 describe a spectrophotometric technique for detecting the presence of glucose using specially selected bands in the near infrared region between 1100 and 2500 nm. Dahne et al. found that by applying light at wavelengths in the 1000–2500 nm range acceptable combinations of sufficient penetration depth to reach the tissues of interest with sufficient sensitivity may be obtained for ascertaining glucose concentration variations without the risk of overheating tissues.

Mendelson et al. in U.S. Pat. No. 5,137,023 also found that wavelengths in the near infrared range are useful for noninvasively measuring the concentration of an analyte such as glucose using pulsatile photoplethysmography. In particular, Mendelson et al. describe a glucose measuring instrument which uses the principles of transmission and reflection photoplethysmography, whereby glucose measurement is made by analyzing either the differences or the ratio of two different near infrared radiation sources that are either transmitted through an appendage or reflected from a tissue surface before and after blood volume change occurs in the systolic and diastolic phases of the cardiac cycle. The technique of photoplethysmography can thus be used to adjust the light intensity to account for errors introduced by excessive tissue absorptions. However, despite the assertions by Dahne et al. and Mendelson et al., the wavelengths in the near infrared (below 2500 nm) are not strongly absorbed by glucose yet are susceptible to interference from other compounds in the blood and thus cannot yield sufficiently accurate measurements.

Rosenthal et al. in U.S. Pat. No. 5,028,787 disclose a noninvasive blood glucose monitor which also uses infrared energy in the near infrared range (600–1100 nm) to measure glucose. However, as with the above-mentioned devices, these wavelengths are not in the primary absorption range of glucose and, accordingly, the absorption at these wavelengths is relatively weak.

A more accurate glucose measuring technique which monitors glucose absorption in its primary absorption range has been proposed by two of the present inventors in U.S. Pat. No. 5,313,941. In that patent, Braig et al. disclose a system for measuring glucose concentration in the middle to far infrared range which provides improved glucose measurements despite the strong tissue absorption that typically attenuates signals in the middle to far infrared range. This is accomplished by passing the long wavelength infrared energy through a finger or other vascularized appendage as short bursts or pulses of energy having a very low duty cycle and low optical bandwidth. The bursts are synchronized with systole and diastole of the cardiac cycle so that only two pulses of energy are sent per heart beat, one during systole and one during diastole. The absorption signals detected during application of the energy bursts are then used to calculate the concentration of the blood constituents using a polynomial equation. The description of the system and method as set forth in U.S. Pat. No. 5,313,941 is hereby incorporated in its entirety by reference.

Infrared emissions from bodies have been used to determine the absolute temperatures of those bodies. For example, some of the present inventors disclose a tympanic thermometer in U.S. Pat. No. 5,159,936 which measures the absolute temperature of the person from the infrared energy emissions of the tympanic membrane. However, such infrared energy emissions have not previously been measured at particular wavelengths to perform constituent absorption measurements.

Accordingly, it is desired to extend the spectroscopic techniques noted above to obtain absorption signals from pulsing arterial blood and to provide more accurate measurements of the concentration of glucose, ethyl alcohol and other blood constituents by overcoming the problems caused by interference from tissues and the like. In particular, a noninvasive blood constituent measuring device is desired which uses long wavelength infrared energy emitted from the person's body for better absorption characteristics and improved signal to noise ratios while also synchronizing long wavelength infrared energy in those emissions with the cardiac cycle so that very accurate, temperature compensated in vivo measurements of the concentrations of such constituents in the arterioles may be made. A method and device for such purposes is described herein.

SUMMARY OF THE INVENTION

The above-mentioned limitations in prior art glucose and other blood constituent measuring devices are overcome by providing an instrument which noninvasively measures the concentration of glucose and other blood constituents in a person's blood by monitoring the infrared absorption of the blood constituent in the blood at long infrared wavelengths were such blood constituents have strong and readily distinguishable absorption spectra. Preferably, the long wavelength infrared energy emitted by the person's body, preferably from a vascularized appendage such as the person's arm, is used as the source of energy for the infrared absorption measurement, which is made without injury, venipuncture or inconvenience to the person. By adjusting the absorption measurement to account for changes in the person's internal temperature, improved accuracy in the glucose readings has been achieved.

Since the person's tissue, water and bone are also strong and variable absorbers of long wavelength infrared energy, the signal to noise ratio in such a system could cause serious errors in the blood constituent concentration measurements. However, potential interference from these sources is overcome in accordance with the present invention by (1) synchronizing the optical transmission measurement with the systolic and diastolic phases of the heart beat and using the resulting expansion and contraction of the arterial walls to isolate the measurement to only arterial blood, and/or (2) using the infrared energy emitted by the person's arm (or other vascularized appendage) which is not readily absorbed by the skin or other tissue as the infrared energy source.

The present inventors have discovered that infrared emissions generated as infrared radiation by a person's tissue when radiated and partially reabsorbed by a blood constituent such as glucose constitutes quantifiable information regarding concentrations of those blood constituents. By using the infrared emissions from the person's body as the source of infrared energy, an infrared source is not necessary, which greatly reduces the energy used and the system complexity, and hence increases the portability of the device. Also, by compensating for variations in the person's internal temperature, improved accuracy has been achieved.

Long wavelength infrared detectors typically have low responsivities because of the attenuation of the signals by the tissues. These problems are addressed by the device of the invention by using infrared emissions from the person's arm or other vascularized appendage for the blood concentration measurement. Thus, in accordance with a presently preferred embodiment of the invention, it is unnecessary to apply high energy infrared energy to the skin of the person, thereby avoiding possible discomfort. Measurements also may be synchronized with systole and diastole in accordance with the invention so as to minimize the adverse interference effects of tissue absorption. In such an embodiment, two or more measurements typically are made per heart beat. An optical plethysmograph or ECG may be used in accordance with the invention to synchronize the measurements with the heartbeat. However, synchronization is not necessary and may be eliminated if it is desired that the spectrophotometer respond to the arterial, venous, and tissue glucose levels simultaneously.

The present invention thus relates to a noninvasive infrared spectrophotometer and method thereof which measures the concentration of at least one predetermined blood constituent, such as glucose or ethyl alcohol, in a person's blood using the infrared emissions from the person's arm or other vascularized appendage as the source of long wavelength infrared energy. In accordance with a preferred embodiment of the invention, such a noninvasive infrared spectrophotometer measures infrared absorption over a broad range of wavelengths of at least 2.0 μm which are emitted as heat by a person. Each constituent to be measured readily absorbs infrared energy at one or more of n wavelengths and minimally absorbs infrared light at one or more other of the n wavelengths within that range. Thus, infrared energy emitted by the person is absorbed by the constituent to be measured, and by measuring this absorption, the concentration of the constituent may be determined. At least one infrared detector detects light at the n wavelengths which has passed through, for example, an arterial blood vessel of the person and been selectively absorbed by the predetermined constituent(s). The infrared detector outputs a detection signal for processing to determine the constituent concentration. A temperature sensing device for measuring the person's internal temperature at the arm or other vascularized appendage is also used in adjusting the constituent concentration measurement for temperature dependent effects.

Synchronizing means may also be provided for synchronizing the measurements with the systolic and diastolic phases of the cardiac cycle of the person. Preferably, the synchronizing means comprises a cardiac monitor and means responsive thereto for controlling absorption measurements to occur during the systolic and diastolic phases of the cardiac cycle of the person. Alternatively, the plethysmograph signal may be obtained from the infrared signal directly, thereby eliminating the need for a separate plethysmograph. In this embodiment, however, the infrared signal still would be gated into systolic and diastolic components.

In addition, a chopper wheel may be used to convert the measured signal to a high frequency in order to overcome the low frequency noise in an HgCdT detector; however, other detectors such as thermopiles do not require a chopper. The chopped signal is then amplified and filtered and synchronously demodulated to recreate the DC signal from the detector without the added noise. The signal is then low pass filtered and passed into the processor for calculation of the concentration of the predetermined constituent(s) from the detection signal to provide a concentration indication which is substantially free of tissue absorption errors.

In a preferred embodiment of a glucose monitor, the detection wavelength is approximately 9.1 μm while the reference wavelength is approximately 10.5 μm. In an alternative embodiment of a blood alcohol monitor, the detection wavelength is approximately 3.4 μm and the reference wavelength is approximately 4.8 μm. Preferably, bandpass analytical filters are also disposed between the arterial blood vessel of the person and the infrared detector(s) for passing infrared light in a narrow passband centered at such detection and reference wavelengths.

Concentration of the predetermined constituent(s) is calculated by forming a ratio R=(Sys L1–Dias L1)/(Sys L2–Dias L2), where Sys L1 is a detected systolic phase signal at the detection wavelength, Dias L1 is a detected diastolic phase signal at the detection wavelength, Sys L2 is a detected systolic phase signal at the reference wavelength, and Dias L2 is a detected diastolic phase signal at the reference wavelength, and then solving the following equation:

$$C.C.=C_1+C_2* Ln(R)+C_3* [Ln(R)]^2+C_4* [Ln(R)]^3+C_5* [Ln(R)]^4,$$

where:
C.C. is the concentration of the predetermined constituent;
$C_1$–$C_5$ are empirically determined calibration coefficients; and
Ln is a natural log function.

The above equation can be generalized for a system using multiple detection wavelengths and one or more reference wavelengths by including cross-product terms in the polynomial.

Also, in the preferred embodiment of the invention, the glucose measurement is compensated for temperature variations in the person's body temperature by measuring the temperature deep within the person's arm or other vascularized appendage. From the measured temperature, $I_o$ is computed to yield a value of the energy level emitted from within the person's arm or other vascularized appendage before the glucose absorbs any infrared energy. The resulting $I_o$ value is then ratioed to the actual measured energy I for computing the percentage of energy absorbed by the glucose. Discontinuities in the ratio are also removed by converting the measured voltages into watts of radiant power, adding the watts emitted by the chopper blade, and then taking the ratio of that quantity. Then, by treating the measured signals from the person's arm or other vascularized appendage as the I value in Beir's equation and ratioing these values to the measured $I_o$ values using Planck's equation, Beir's law may be rewritten to allow for compensation for temperature dependencies as:

$$I/I_o = e^{-CLX},$$

where C is the glucose concentration, L is the pathlength from where the infrared emissions originate to where they are detected, X is an experimentally determined extinction coefficient, I is the energy emitted by the arm, and $I_o$ is the incident energy within the arm, defined from Planck's equation as:

$$I_o = T_R * \epsilon * \frac{C_1}{\lambda^5 \left(e^{\frac{C_2}{\lambda T}} - 1\right)}$$

where $T_R$ is the transmission coefficient of the selected filter, $\epsilon$ is the emissivity of skin, $C_1=3.74\times10^4$, $C_2=1.438\times10^4$, T is the measured absolute temperature deep within the body or arm, and $\lambda$ is the wavelength of the selected filter.

BRIEF DESCRIPTION OF THE DRAWINGS

The objects and advantages of the invention will become more apparent and more readily appreciated from the following detailed description of presently preferred exemplary embodiments of the invention taken in conjunction with the accompanying drawings, of which.

DETAILED DESCRIPTION OF THE PRESENTLY PREFERRED EMBODIMENTS

A noninvasive infrared spectrometer with the abovementioned beneficial features in accordance with the presently preferred exemplary embodiment of the invention will now be described with reference to FIGS. 1–5. It will be appreciated by those of ordinary skill in the art that by changing the wavelengths of infrared energy to be monitored for absorption that other blood constituents such as ethyl alcohol, carbon dioxide, urea, uric acid, lipids, creatinine, peptides, cholesterol, hematocrit, drugs, and several other analytes can be measured in accordance with the techniques of the invention. Thus, the glucose monitoring device described herein in the exemplary embodiments is for descriptive purposes only and is not intended in any way to limit to scope of the invention. All questions regarding the scope of the invention may be resolved by referring to the appended claims.

As known by those skilled in the art, most covalent bonds have characteristics and essentially invariant absorption wavelengths so that the presence of an absorption band in the infrared spectrum indicates the presence of a bond in the molecule while the absence of an absorption peak guarantees the absence of its corresponding bond. Hence, each compound or blood constituent measured in accordance with the techniques of the invention has a characteristic absorption spectrum in the infrared range which may be used to establish one or more detection and reference wavelengths for absorption measurement. Glucose measurement in the far infrared range will be described herein as a presently preferred embodiment, although the present invention also has particular utility as a blood alcohol monitor in the middle and far infrared ranges.

The infrared spectra includes the near infrared (approximately 1 to 3 microns), the middle infrared (approximately 3–6 microns), the far infrared (approximately 6–15 microns), and the extreme infrared (approximately 15–100 microns). As noted above, typical glucose and other noninvasive blood constituent measuring devices operate in the near infrared region where the absorption of infrared energy by glucose and other blood constituents is relatively low. However, the present inventors have found a technique whereby absorption may be measured in the middle and far infrared regions where glucose and other blood constituents have strong and distinguishable absorption spectra while also minimizing the adverse effects of tissue, water and bone absorption.

Glucose has strong characteristic spectra in the far infrared above about 6 microns. As described by Mueller in WO 81/00622, glucose absorption may be measured using a detection wavelength at approximately 9.1 µm and a reference wavelength at approximately 10.5 µm. Similarly, ethyl alcohol has a strong characteristic spectra in the middle infrared (3–4 µm) and in the far infrared (9–10 µm). Accordingly, ethyl alcohol concentration may be measured using a detection wavelength of approximately 3.4 microns and a reference wavelength of approximately 4.8 microns using differential absorption calculation techniques.

Figure 1:
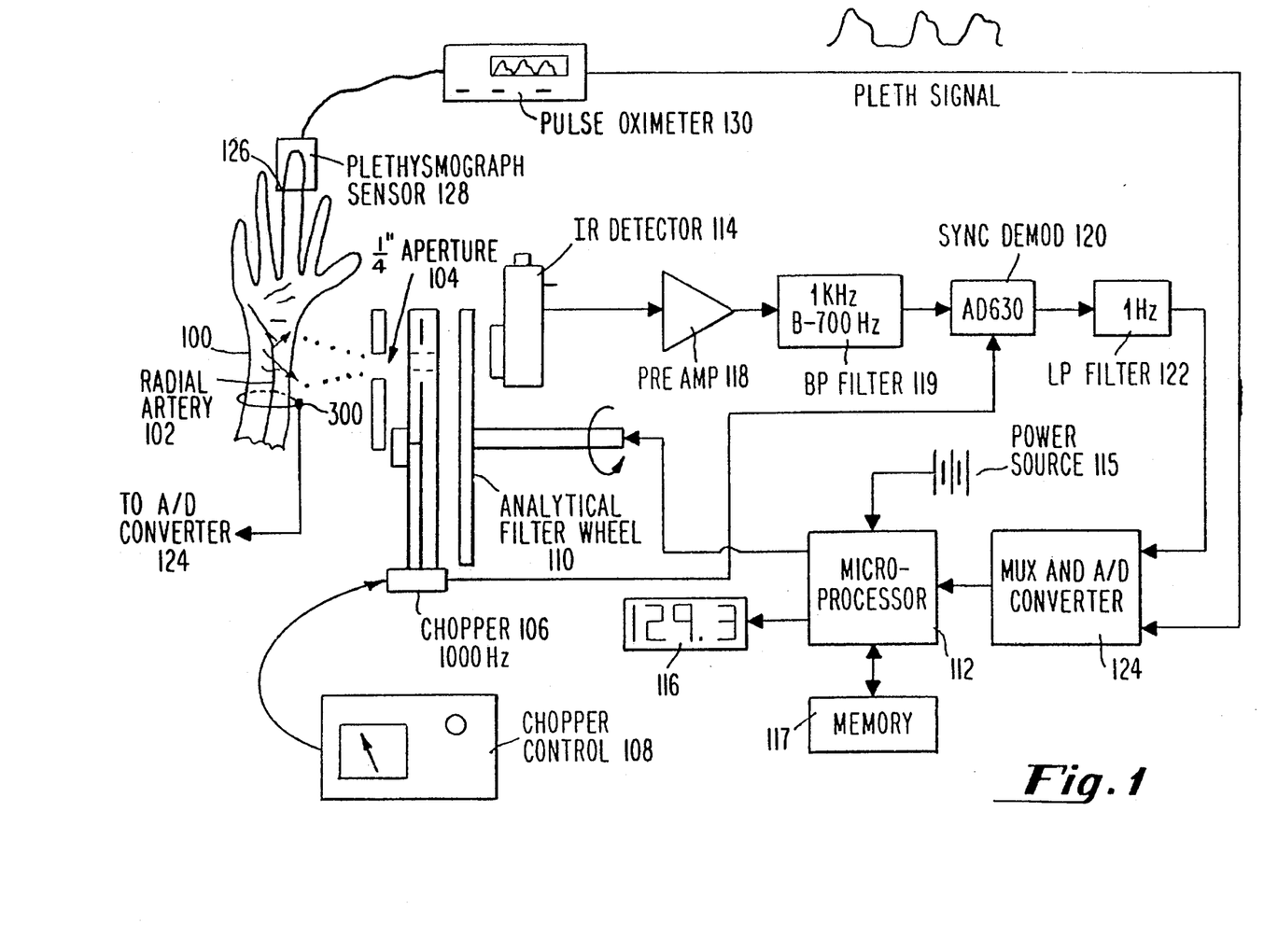
FIG. 1 schematically illustrates a preferred embodiment of a noninvasive infrared spectrophotometer in which infrared energy emitted by the person is used as the infrared energy source.

FIG. 1 illustrates a "self-emission" glucose monitor which noninvasively measures the concentration of glucose and/or other constituents in a person's blood by monitoring the infrared emission of glucose in the blood at long infrared wavelengths near 10 microns. In other words, unlike prior art analyzers or the analyzer described in U.S. Pat. No. 5,313,941, the present embodiment of the invention does not include an infrared source and instead utilizes the infrared energy emitted by the person's blood and/or surrounding tissue to perform the absorption analysis.

The inventors have found that in prior art "infrared transmission" type analyzers only a small amount of signal passes through the selected appendage. By contrast, in accordance with the presently preferred embodiment, the infrared source is no longer needed since the normal body heat provides the source of infrared energy. However, analysis is still performed at the longer wavelengths of infrared energy. In particular, wavelengths between 2 and 12 microns are particularly preferred because these wavelengths are naturally emitted by the body as the wavelengths of heat, and because molecular absorption in the 2–12 micron region is very molecule specific. As noted in U.S. Pat. No. 5,313,941, this region contains the "fingerprint" region in analytical chemistry because in this region each molecule has a distinct absorption spectra.

This embodiment of the invention thus requires no source of energy other than the human body. No energy is passed through an appendage, thereby eliminating any possible danger associated with excessive radiation. Because it is unnecessary to generate optical energy, the present embodiment operates on less power, thus making this embodiment a more likely candidate for portable operation.

As illustrated in FIG. 1, the invention of the preferred embodiment preferably includes an infrared detection device which is designed to rest on the underside of a person's wrist 100 for detection of infrared heat energy emitted from the interior 102 of the person's arm. The detector includes a ¼ inch aperture 104 which passes the infrared signal from the interior 102 of the person's arm (or other vascularized appendage) to a chopper 106 controlled by a chopper control device 108 for converting the signal to a high frequency in order to minimize the low frequency noise in the detector. The signal then passes through a filter wheel 110 containing the analytical and reference filters for making the absorption measurements in accordance with the techniques described below. Analytical filter wheel 110 is controlled by microprocessor 112 to control detection of the absorption of the desired constituents or the reference by infrared detector 114. In a preferred embodiment, the filter wheel 110 changes filters every 3 heartbeats.

Microprocessor 112 receives energy from an AC or DC power source 115 which preferably permits the invention to be miniaturized for use in a hand-held monitor. The calculated concentration is then displayed on display 116 so that the user may readily ascertain his or her glucose level, ethyl alcohol level, and the like. Microprocessor 112 preferably further includes memory 117 for storing sequences of such measurements so that averaging and trending and the like may be conducted.

In a presently preferred embodiment, a cooled HgCdT detector is used as infrared detector 114. The cryogenic cooling of such a detector enhances the infrared signal since infrared detectors generally respond to the difference in temperature between the target (in this case the interior 102 of the person's arm) and the detector. However, with low noise electronics and appropriate signal processing, room temperature detectors such as the thermopile and pyroelectric types used in the detector described in U.S. Pat. No. 5,313,941 also may be used in this embodiment.

Upon detection, the chopped and filtered signal is amplified by preamplifier 118 and then filtered by bandpass filter 119 to minimize noise before the signal is demodulated by synchronous demodulator 120. Synchronous demodulator 120 demodulates the chopped signal to recreate the DC signal from the detector, only now the noise is substantially reduced. The signal is then low pass filtered by low pass filter 122 and passed to multiplexer and A/D converter 124 for processing in accordance with the techniques described below.

As with the monitor described in U.S. Pat. No. 5,313,941, the monitor of this embodiment is designed to analyze arterial blood metabolite levels. By monitoring the cardiac pulse and synchronizing to that pulse, arterial blood signals can be discriminated from other signals. In this embodiment, the infrared detector 114 continuously measures the infrared energy emitted from the interior 102 of the person's arm, for example. As with the monitor described in U.S. Pat. No. 5,313,941, in this embodiment an optical plethysmograph monitors the person's pulse very near the infrared signal site. As shown in FIG. 1, the plethysmograph signal preferably is taken from the person's middle (or ring) finger 126 by plethysmograph sensor 128 while the infrared signal is taken from the underside of the person's wrist 100. The plethysmograph signal is then applied to synchronous demodulation electronics in a preamplifier of a pulse oximeter or other cardiac monitor 130, which converts the silicon detector output into a useful signal. The resulting plethysmograph signal is applied to multiplexer and A/D converter 124 and then to microprocessor 112 for processing in accordance with the techniques described below. The plethysmograph signal is used to electronically gate the infrared signal from the underside of the wrist 100 into systolic and diastolic signals to help minimize tissue absorption effects. Since veins and tissues generally do not pulse, their contribution to the detected signal is cancelled when the ratio is taken.

Figure 2:
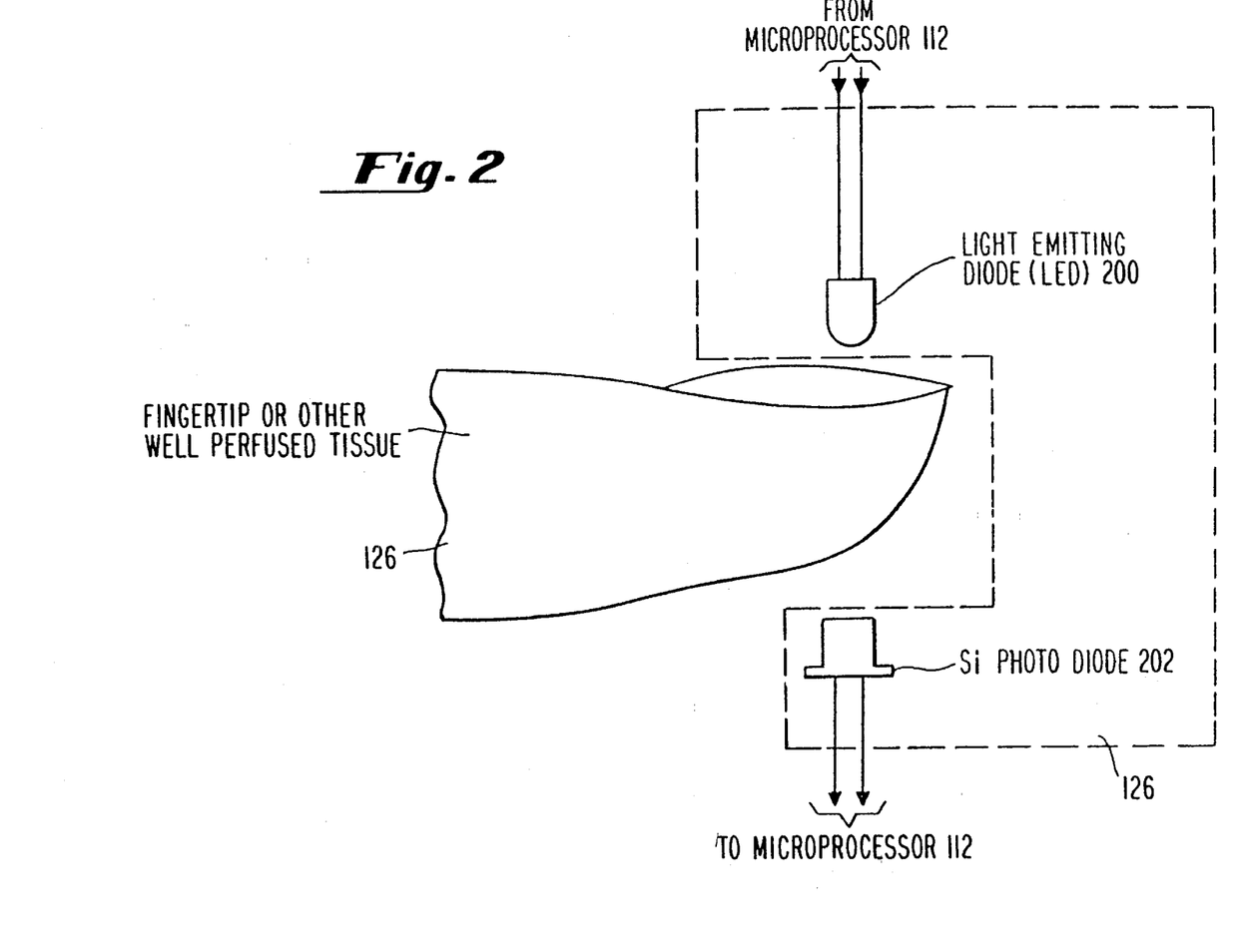
FIG. 2 illustrates a photoplethysmograph for detecting systole and diastole in the embodiment of FIG. 1.

During operation, an LED of plethysmograph sensor 128 is located on the middle (or ring) finger 126 of the person, thereby forming a visible or near infrared light source 200 as shown in FIG. 2. The LED 200 is pulsed by microprocessor 112 and LED driver circuits (not shown). The signal from LED 200 passes through the finger 126 and is detected by silicon photo diode 202. As noted above, synchronous demodulation electronics in a preamplifier of the cardiac monitor 130 convert the silicon detector output into a useful signal. The LED 200, silicon photo diode 202, and preamplifier circuit of the cardiac monitor 130 together constitute an optical plethysmograph. As described in detail in U.S. Pat. No. 5,313,941, the plethysmograph signal is used by microprocessor 112 to determine the phase of the cardiac cycle for controlling the gating of the infrared signal into systolic and diastolic integrators within the software of microprocessor 112.

In an alternative embodiment to the embodiment of FIGS. 1 and 2, the plethysmograph signal is obtained from the infrared signal directly so as to eliminate the need for a separate plethysmograph. In such an embodiment, the infrared signal is still gated into systolic and diastolic components; however, the plethysmogram is derived from the infrared signal itself rather than a separate plethysmograph. Of course, other techniques for monitoring the cardiac cycle maybe used. For example, the cardiac monitor 130 may utilize an electrocardiogram for synchronizing to a characteristic feature of the electrocardiogram.

On the other hand, those skilled in the art will appreciate that synchronization to the cardiac cycle is not strictly necessary and that the synchronization step may be eliminated. Without synchronization, the spectrophotometer of the invention will respond to arterial, venous, and tissue glucose levels simultaneously, which may be desired in some circumstances.

Thus, in accordance with the invention, if the spectrophotometer is to be synchronized to the cardiac cycle, the following steps are performed. In particular, microprocessor 112 electively processes the plethysmograph signal from photodetector 202 in order to determine systole and diastole in the next cardiac cycle as follows:

1. A conventional plethysmograph signal is obtained by photodetector 202, digitized by analog to digital converter 124 and recorded in memory 117 as pulse N-1. This is accomplished by dividing the plethysmograph signal N-1 into sampling intervals having durations of approximately 0.1 to 10 msec. Preferably, the plethysmograph signal from photodetector 202 is sampled by analog to digital converter 124 every 1 msec.

2. A characteristic feature of the cardiac cycle waveform is selected for purpose of synchronization. Preferably, the dicrotic notch, which is a feature on the waveform of the cardiac cycle where a distinctive dip occurs as a result of the closing of the ventricular valves in the heart, is selected and labelled as time zero for cycle N-1. All other 1 msec intervals occurring after the dicrotic notch are labelled as one, two, three, etc. until the next dicrotic notch for the cycle N is found.

3. The waveform N-1 is then examined to find the peak signal point (systole) and the interval number (i.e., the number of intervals or msec from the dicrotic notch) is stored.

4. The waveform N-1 is then examined to find the minimum signal point (diastole) and the interval number is also stored.

5. In cardiac cycle N, running in real time, the dicrotic notch is again identified. The interval number stored in step 4 for pulse N-1 is then counted from the dicrotic notch to determine the time interval anticipated to correspond to diastole for cycle N. The infrared energy from underside of the person's wrist 100 is then measured during a 2 millisecond interval around diastole. At the end of this 2 millisecond interval, the appropriate number of intervals is counted to determine the time interval anticipated to correspond to systole in cycle N. The infrared energy from the underside of the person's wrist 100 is measured again for approximately 2 milliseconds around systole.

6. The absorption signals developed by the infrared detector 114 are digitized by analog to digital converter 124 and stored in memory 117 or another temporary register of microprocessor 112.

7. In cycle N, the infrared LED plethysmograph signal is again recorded and examined. If is determined that systole and diastole occurred within approximately +/−10 msec of where they were predicted to have occurred during analysis of pulse N-1, the long wavelength infrared data stored in memory 117 or some other temporary register is then passed to the glucose processing algorithm of microprocessor 112 for calculation of the glucose concentration. However, if systole and diastole did not occur within +/−10 msec of where they were predicted to have occurred in cycle N-1, the stored values are erased from memory 117.

8. Steps 1–7 are then repeated until a number of usable measurements have been made. The measurements may then be averaged or the highest and lowest values thrown out so that an accurate calculation of concentration may be made by microprocessor 112 and displayed on display device 116.

Measurement of the infrared detection signal may be synchronized with the heart beat as just described in order to remove the effects of tissue and other "non pulsating" interferants sometimes referred to as patient variations. However, heart beats are not the same every time and vary from individual to individual. These variations present a challenge to calibration of an instrument. Accordingly, in order to normalize the absorption readings and overcome the requirement for individual calibrations, at least two long infrared wavelengths are measured simultaneously during diastole and systole as just described. As described above, for glucose the analytical wavelength specifically absorbed by glucose is preferably in the range of approximately 9.1 μm, while the reference wavelength is preferably in the range of approximately 10.5 μm, which is not absorbed by glucose. Generally, glucose concentration is determined by forming a ratio between the systolic and diastolic difference signals measured at 9.1 μm versus those measured at 10.5 μm. More than one reference and analytical wavelength may be used so that multiple ratios are formed. The resulting arrays of numbers are then operated upon by empirically determined calibration coefficients. The resulting computation yields the concentration of glucose in the person's arterial blood.

The general form of the mathematics used by microprocessor 112 for calculating the concentration of a blood component such as glucose from absorption signals generated at two or more wavelengths in accordance with the techniques of the invention will now be described.

In general, for a system of n+1 detection wavelengths for detecting n blood constituents such as glucose, alcohol and the like, where the systolic phase signal at wavelength n is SYS LN and the diastolic phase signal at wavelength n is DIAS LN, the concentration of the blood component (such as glucose) being measured can be computed as a mathematical function of SYS LN and DIAS LN. For example, the component concentration (C.C.) may be represented as:

$$C.C. = Fn\ (SYS\ LN,\ DIAS\ LN).$$

For a system using multiple-(at least two) wavelengths where L1 –LN are analytical wavelengths and LR is one or more reference wavelengths, then:

$$R_N = (SYS\ LN - DIAS\ LN)/(SYS\ LR - DIAS\ LR);\quad EQ.\ (1)$$

Of course, other mathematical forms of the ratio R may be used, but in general, $R_N = FN\ (LN, LR)$.

The concentration of each blood constituent is then a function of each ratio R for that constituent. For example, glucose concentration (G.C.) may be calculated from a polynomial equation of order p for a single detection and a single reference wavelength as:

$$G.C. = C_1 + C_2 * Ln(R) + C_3 * [Ln(R)]^2 + C_4 * [Ln(R)]^3 + C_5 * [Ln(R)]^4,\quad EQ.\ (2)$$

where $C_1$–$C_5$ are calibration constants, Ln is the natural log function and p=4. However, when plural detection wavelengths and/or plural reference wavelengths are used, cross-product terms would be added, resulting in the following generalized equation:

$$C.C._n = B + \sum_{x=1}^{x=(m-1)} \left[ \sum_{y=1}^{y=p} C_{x,y} * [Ln(R_x)]^y \right] + \sum_{z=1}^{z=p} D_z * [Ln(R_1) * Ln(R_2) \ldots * Ln(R_n)]^z\quad EQ.\ (3)$$

where B, $C_{x,y}$, and $D_z$ are calibration constants, m is the total number of analytical and reference wavelengths (m>=(n+1)) and Ln in the natural log function.

Of course, other equations besides a polynomial equation may be used by those skilled in the art to calculate the concentration of the respective blood constituents. For example, the systolic/diastolic ratios may be replaced with their logarithms as in pulse oximeter computations. Alternatively, the mathematical technique known as "chemometrics" may be used to provide a multiple wavelength spectral analysis.

As is apparent from the above, measurement of concentrations by optical absorption involves making measurements of absorbed light and applying some derivation of Beir's law to compute the concentration, where Beir's law can be stated as $I = I_o * e^{-CLX}$, where C is the glucose concentration, L is the pathlength from where the infrared emissions originate to where they are detected, X is an experimentally determined extinction coefficient, I is the energy emitted by the arm, and $I_o$ is the incident energy within the arm, defined from Planck's equation as:

$$I_o = T_R * \epsilon * \frac{C_1}{\lambda^5 \left( e^{\frac{C_2}{\lambda T}} - 1 \right)}\quad EQ.\ (4)$$

where $T_R$ is the transmission coefficient of the selected filter, $\epsilon$ is the emissivity of skin, $C_1 = 3.74 \times 10^4$, $C_2 = 1.438 \times 10^4$, T is the measured absolute temperature deep within the body or arm, and $\lambda$ is the wavelength of the selected filter. Accordingly, the computation of C, the concentration of interest, usually involves measuring I and $I_o$ and solving Beir's equation for C.

However, in a system of the type proposed above in which the energy emitted from within the body of a subject is measured, an optical measurement of $I_o$, the incident energy, is not possible because the energy can only be sensed after it has passed through the skin and substance to be measured. However, the present inventors have now discovered that Planck's Equation may be used to compute the actual value of $I_o$ based on the temperature of the source of radiation, in this case, the person's arm. As known by those skilled in the art, Planck's equation gives the radiant emittance of a "blackbody" at a particular wavelength and temperature and can be written as:

$$W_\lambda = \frac{C_1}{\lambda^5 \left( e^{\frac{C_2}{\lambda T}} - 1 \right)}\quad EQ.\ (5)$$

where W=watts/cm² per micron of wavelength, $\lambda$=wavelength in microns, T=absolute temperature in degrees Kelvin, $C_1 = 3.74 * 10^4$, $C_2 = 1.438 * 10^4$, and $W_\lambda$=radiant flux emitted per unit area per unit increment of wavelength in watts/cm²-micron.

To correct for temperature dependent effects, $I_o$ is computed using Equation (4) to yield a value of the energy level emitted from within the target (person's arm) before the glucose absorbs any energy. The computed value for $I_o$ is then ratioed to the actual measured energy I for computation of the percentage of energy absorbed by the glucose. By ratioing, many of the terms, such as the pathlength L, effectively drop out of the equation.

Figure 3:
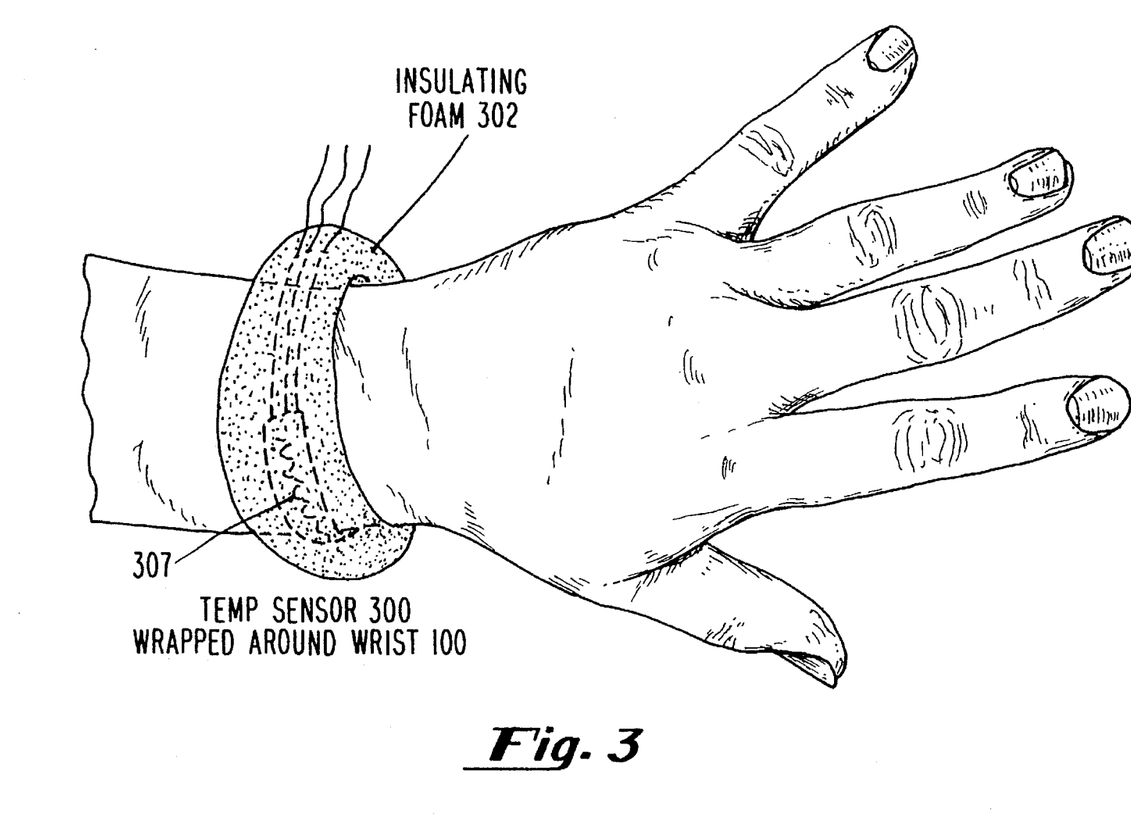
FIG. 3 illustrates a temperature sensing device for determining the internal arm temperature for temperature compensation of the glucose readings in accordance with the invention.
Figure 4:
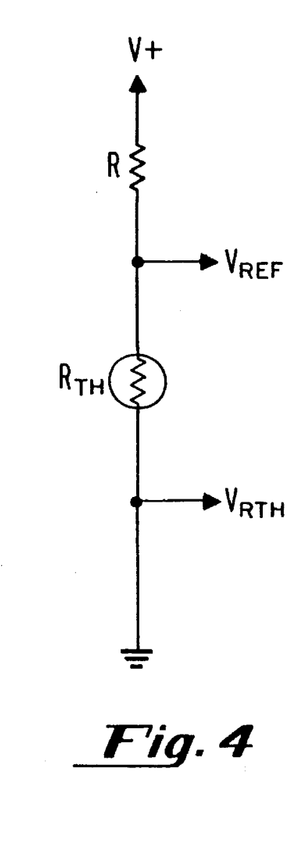
FIG. 4 is a circuit diagram of the temperature sensing circuit of FIG. 3.

Thus, to compute $I_o$, it is necessary to measure the temperature deep within the person's body. For this purpose, a temperature sensor 300 (FIG. 3) may be placed, for example, around the person's wrist for measurement of the internal temperature of the person's arm. As shown in FIG. 3, the temperature sensor 300 may include a flexible rectangular RTD such as MINCO part #S386PD10Z36A which is wrapped around the person's wrist 100 or forearm and covered with an insulating elastic foam 302, such as TRU-FIT model 405 Neoprene Wrist Support. As shown in FIG. 4, the temperature sensing element (RTH) 301 is electrically connected in series with a precision resistor (R). Two voltage measurements $V_{ref}$ and $V_{rth}$ are made, and a linear equation is used to determine the temperature from the voltage ratio $V_{rth}/V_{ref}$. Once the temperature is known, Equation (4) is used to compute $I_o$ in units of watts.

Figure 5:
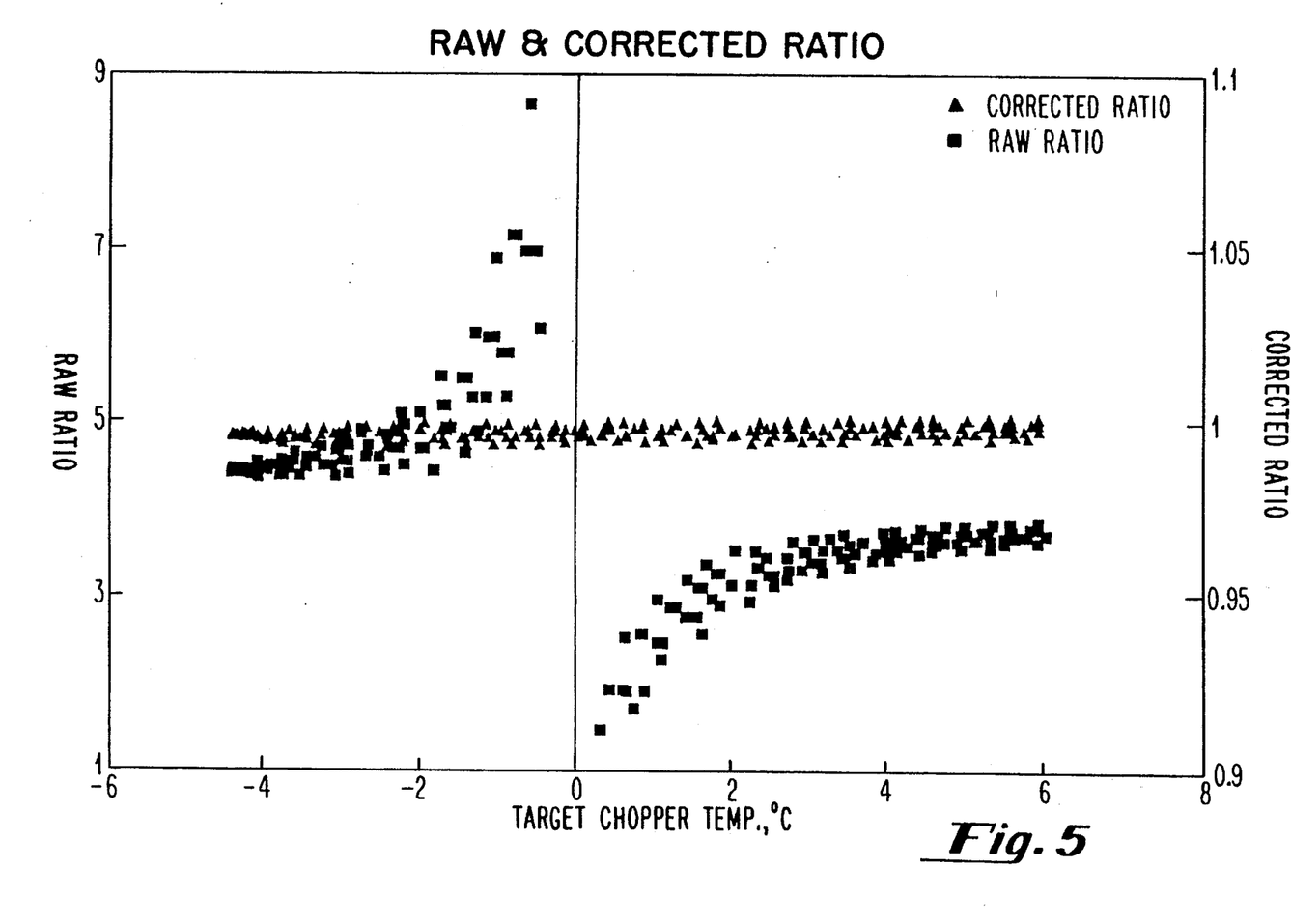
FIG. 5 is a graph illustrating the ratio of target wattage at 9.4 μm divided by the target wattage at 10.5 μm before and after correction of the temperature dependent effects and discontinuity at zero.

One of the problems associated with taking the ratios of the 9.4 and 10.5 micron signals when applying such techniques to the monitor of FIG. 1 has been that the ratio "blew up" and became discontinuous as the signals approached zero and/or went negative. Whenever the target is at a lower temperature than the chopper wheel 106, the measured signal would be less than zero. When the target temperature equals the temperature of the chopper wheel 106, the signals will also equal zero. On the other hand, when the target is warmer than the chopper wheel 106, a positive signal is produced. As shown in FIG. 5, the ratio of the 9.4 signal to the 10.5 signal results in a discontinuity at zero delta temperature. Since the ratio is what is used to compute glucose concentration, it is desired to remove this discontinuity.

To eliminate the discontinuity, the voltages measured are converted into watts of radiant power and the ratio is taken of that quantity. The conversion takes two steps:

1. Convert measured voltage to watts; and
2. Add the watts emitted by the chopper blade 106. Step two is required because the system of the preferred embodiment is only responsive to the difference between the temperature of the chopper wheel 106 and the target temperature as determined by temperature sensor 300.

Conversion of the measured voltage to wattage is accomplished by calibrating the system experimentally. A linear regression may be used to convert the voltage produced by the detector to the wattage predicted by Planck's equation. After the measured wattage is known, the wattage emitted from the chopper wheel 106 is computed using Planck's equation. Then, since the measured wattage equals the target-chopper voltage, the chopper wattage is added to the measured wattage to yield target wattage. Now, when the ratio of target wattage at 9.4 microns is divided by the target wattage at 10.5 microns, the discontinuity is eliminated.

As shown in FIG. 5, while the ratio discontinuity is no longer a problem, the ratio shows a strong dependence with temperature. Removing this dependence will allow for the computation of more accurate glucose concentrations.

The temperature dependence is caused by the shifts in the peak and shape of the black body radiation curve with temperature. Planck's Equation described this emission spectra. As noted above, Planck's Equation and the measured temperatures can be used to compute the theoretical $I_o$ value. If the measured signals are then treated as the I value in Beir's equation and ratioed to the $I_o$ values from Planck's equation, Beir's law may be rewritten as $I/I_o = e^{-CLX}$, as noted in Equation (4) above.

To apply the theory, a measurement of the ratio may be taken from a glucose solution soaked chamois. The target temperature is swung over a wide range to test the temperature correction to its fullest. FIG. 5 shows the pre and post correction ratios. The right scale is for the temperature corrected ratio, while the left scale is for the "raw ratio". As shown, the discontinuity at zero and the temperature dependencies in the ratio have been eliminated. These techniques are thus desirably used in the calculation noted above to eliminate such potential errors in the computations.

The amplitude of the signal detected by the infrared detector 114 establishes the signal to noise ratio of the entire system. The larger the signal, the lower the system noise. Lower system noise leads to shorter integration times and faster measurements. In accordance with the present embodiment, the signal output by detector 114 has been measured to be approximately 8 nV per mg/dl. The raw signal has been measured at 65 microvolts with a pulse amplitude of 1% of the DC signal. While those skilled in the art will appreciate that such a signal is sufficient to make a meaningful measurement, it is desirable to increase the pulse amplitude to improve the signal to noise ratio. One such technique in accordance with the invention includes inflating a blood pressure cuff in synchrony with the glucose measurement.

As noted above, preferred embodiments of the invention described herein are specifically designed to monitor glucose which absorbs selectively near 9.1 μm. However, those skilled in the art will appreciate that by changing the wavelengths of infrared energy detected other bloodstream constituents such as carbon dioxide, ethyl alcohol, urea, uric acid, lipids, creatinine, peptides, cholesterol, hematocrit, drugs (all absorbing in the 5–10 μm band) and several other analytes can be measured. Also, the dialysis fluid of kidney patients may be monitored using the techniques of the invention.

The invention herein described offers both specificity and noninvasive measurement, thereby making it acceptable for use by anyone needing to measure or monitor his or her blood glucose level, ethyl alcohol level or other blood constituents levels. Use of long wavelength infrared absorbance measurements provide signals at the exact wavelengths absorbed specifically and strongly by glucose or some other blood constituent, while use of pulsed and cardiac synchronized infrared energy bursts removes interference effects caused by tissue absorption yet provides for a high energy infrared signal without discomfort.

Although an exemplary embodiment of the invention has been described in detail above, those skilled in the art will readily appreciate that many additional modifications are possible in the exemplary embodiment without materially departing from the novel teachings and advantages of the invention. For example, the present invention may be used to measure other blood constituents such as those mentioned herein by selecting one or more analytical wavelengths and one or more reference wavelengths using techniques known to those skilled in the art. Accordingly, these and all such modifications are intended to be included within the scope of the invention as defined in the following claims.

We claim:

1. A noninvasive infrared spectrophotometer, comprising:
   means for detecting infrared emissions generated and emitted by a vascularized appendage of a person;
   means for determining infrared absorption of at least one predetermined constituent of the person's blood from said infrared emissions detected by said detecting means;
   means for measuring an internal temperature of said person at a point of said vascularized appendage where said infrared emissions are detected by said detecting means; and
   processing means for determining the infrared emissions corresponding to said internal temperature measured by said temperature measuring means and for calculating a concentration of said at least one predetermined constituent as a function of the infrared emissions detected by said detecting means and the determined infrared emissions corresponding to said internal temperature measured by said temperature measuring means.

2. A spectrophotometer as in claim 1, further comprising synchronizing means for synchronizing the detection of said infrared emissions by said detecting means with systolic and diastolic phases of a cardiac cycle of the person.

3. A spectrophotometer as in claim 1, wherein said temperature measuring means comprises an RTD which is adapted to be wrapped around the person's arm.

4. A spectrophotometer as in claim 3, wherein said temperature measuring means further comprises an insulating material adapted to be wrapped around the person's arm so as to cover said RTD.

5. A spectrophotometer as in claim 1, wherein said processing means calculates the concentration C of said at least one predetermined constituent in accordance with the equation:

$$I/I_o = e^{-CLX},$$

where L is a pathlength from a point within said vascularized appendage where said infrared emissions originate to said detecting means, X is an experimentally determined extinction coefficient, I is the infrared emissions detected by said detecting means, and $I_o$ is the incident energy within said vascularized appendage, defined from Planck's equation as:

$$I_o = T_R * \epsilon * \frac{C_1}{\lambda^5 \left( e^{\frac{C_2}{\lambda T}} - 1 \right)}$$

where $T_R$ is a transmission coefficient of a filter which passes said at least one predetermined constituent, $\epsilon$ is emissivity of skin, $C_1 = 3.74 \times 10^4$, $C_2 = 1.438 \times 10^4$, T is the internal temperature of said person at said point where said infrared emissions originate, and $\lambda$ is a wavelength of said filter.

6. A noninvasive infrared spectrophotometer for determining a concentration of at least one predetermined constituent in a person's blood, comprising:

means for detecting infrared energy generated and emitted by the person in a wavelength range including n different wavelengths of at least 2.0 µm, said infrared energy containing energy at each of said n wavelengths which is differently absorbed by said at least one predetermined constituent whereby each predetermined constituent readily absorbs infrared energy at least one of said n wavelengths and minimally absorbs infrared energy at another of said n wavelengths, said detecting means outputting at least one detection signal representative of infrared energy at said n wavelengths which has been emitted by said person and selectively absorbed by said at least one predetermined constituent;

means for measuring an internal temperature of said person at a point of said person where said infrared energy is detected by said detecting means; and processing means for determining the infrared emissions corresponding to said internal temperature measured by said temperature measuring means and for calculating the concentration of said at least one predetermined constituent as a function of the infrared energy detected by said detecting means and the determined infrared emissions corresponding to said internal temperature measured by said temperature measuring means.

7. A spectrophotometer as in claim 6, wherein said infrared energy is detected by said detecting means during a diastolic time interval of a diastolic phase of the cardiac cycle of the person and during a systolic time interval of a systolic phase of the cardiac cycle of the person, said systolic and diastolic time intervals each having a duration of approximately 0.1–10 msec during the systolic and diastolic phases, respectively, of said cardiac cycle of the person.

8. A spectrophotometer as in claim 6, wherein said at least one predetermined constituent includes glucose, said one wavelength is approximately 9.1 µm and said another wavelength is approximately 10.5 µm.

9. A spectrophotometer as in claim 8, further comprising an analytical filter wheel including first and second bandpass filters disposed between an arterial blood vessel of the person and said detecting means, said first bandpass filter passing infrared light in a narrow passband centered at approximately 9.1 µm, and said second bandpass filter passing infrared light in a narrow passband centered at approximately 10.5 µm.

10. A spectrophotometer as in claim 8, further comprising a first bandpass filter disposed between an arterial blood vessel of the person and said detecting means, said first bandpass filter passing infrared light in a narrow passband centered at approximately 9.1 µm, and a second bandpass filter disposed between the arterial blood vessel of the person and said detecting means, said second bandpass filter passing infrared light in a narrow passband centered at approximately 10.5 µm.

11. A spectrophotometer as in claim 6, wherein said at least one predetermined constituent includes ethyl alcohol, said one wavelength is approximately 3.4 µm and said another wavelength is approximately 4.8 µm.

12. A spectrophotometer as in claim 11, further comprising an analytical filter wheel including first and second bandpass filters disposed between an arterial blood vessel of the person and said detecting means, said first bandpass filter passing infrared light in a narrow passband centered at approximately 3.4 µm, and said second bandpass filter passing infrared light in a narrow passband centered at approximately 4.8 µm.

13. A spectrophotometer as in claim 11, further comprising a first bandpass filter disposed between an arterial blood vessel of the person and said detecting means, said first bandpass filter passing infrared light in a narrow passband centered at approximately 3.4 µm, and a second bandpass filter disposed between the arterial blood vessel of the person and said detecting means, said second bandpass filter passing infrared light in a narrow passband centered at approximately 4.8 µm.

14. A spectrophotometer as in claim 6, further comprising synchronizing means for synchronizing the detection of said infrared energy by said detecting means with systolic and diastolic phases of a cardiac cycle of the person.

15. A spectrophotometer as in claim 14, wherein said synchronizing means includes a cardiac monitor and plethysmograph sensing means for detecting said systolic and diastolic phases of the cardiac cycle of the person from well perfused tissue of the person.

16. A spectrophotometer as in claim 15, wherein said plethysmograph sensing means comprises a pulsed light emitting diode which directs light through said well perfused tissue of the person and a photodetector which detects the light which has passed through said well perfused tissue of the person, and said cardiac monitor comprises processing means for processing a detection output of said photodetector to determine a phase of said cardiac cycle.

17. A spectrophotometer as in claim 6, wherein said processing means calculates the concentration C of said at least one predetermined constituent in accordance with the equation:

$$I/I_o = e^{-CLX},$$

where L is a pathlength from a point within said person where said infrared energy originates to said point where said infrared energy is detected by said detecting means, X is an experimentally determined extinction coefficient, I is the infrared energy detected by said detecting means, and $I_o$ is the incident energy within said person where said internal temperature is measured, defined from Planck's equation as:

$$I_o = T_R * \epsilon * \frac{C_1}{\lambda^5 \left( e^{\frac{C_2}{\lambda T}} - 1 \right)}$$

where $T_R$ is a transmission coefficient of a filter which passes said at least one predetermined constituent, $\epsilon$ is emissivity of skin, $C_1 = 3.74 \times 10^4$, $C_2 = 1.438 \times 10^4$, T is the internal temperature of said person at said point of said person where said infrared energy originates, and $\lambda$ is a wavelength of said filter.

18. A spectrophotometer as in claim 6, further comprising a chopper wheel which modulates said infrared energy emitted by the person to a frequency beyond baseband prior to detection by said detecting means, a preamplifier which amplifies said at least one detection signal, a bandpass filter centered at said frequency beyond baseband, and a synchronous demodulator which demodulate said demodulation signal from said frequency beyond baseband.

19. A spectrophotometer as in claim 18, wherein said processing means forms a ratio R=(Sys L1−Dias L1)/(Sys L2−Dias L2), where Sys L1 is a detected systolic phase signal at said one wavelength, Dias L1 is a detected diastolic phase signal at said one wavelength, Sys L2 is a detected systolic phase signal at said another wavelength, and Dias L2 is a detected diastolic phase signal at said another wavelength.

20. A spectrophotometer as in claim 19, wherein said processing means converts said ratio R from a voltage reading to a reading in watts and adds watts of infrared energy emitted by said chopper wheel to determine a temperature difference between said internal temperature and said chopper wheel, thereby eliminating discontinuities in said ratio R.

21. A method of noninvasively measuring a concentration of at least one predetermined, constituent in a person's blood, comprising the steps of:

detecting infrared emissions generated and emitted by a person;

detecting a temperature of said person at a point of emission of the infrared emissions detected in said infrared emissions detecting step;

determining infrared absorption of at least one predetermined constituent of a person's blood using said infrared emissions detected in said infrared emissions detecting step;

determining the infrared emissions corresponding to said temperature measured in said temperature measuring step; and calculating the concentration of said at least one predetermined constituent as a function of the infrared emissions detected in said infrared emissions detecting step and the determined infrared emissions determined in infrared emissions determining step.

22. A method as in claim 21, comprising the further step of synchronizing the detection of said infrared emissions with systolic and diastolic phases of a cardiac cycle of the person.

23. A method as in claim 21, wherein said calculating step comprises the step of calculating the concentration C of said at least one predetermined constituent in accordance with the equation:

$$I/I_o = e^{-CLX},$$

where L is a pathlength from said point of infrared emissions to a detection point, X is an experimentally determined extinction coefficient, I is the detected infrared emissions, and $I_o$ is the incident energy within said person at said point of emission, defined from Planck's equation as:

$$I_o = T_R * \epsilon * \frac{C_1}{\lambda^5 \left( e^{\frac{C_2}{\lambda T}} - 1 \right)}$$

where $T_R$ is a transmission coefficient of a filter which passes said at least one predetermined constituent, $\epsilon$ is emissivity of skin, $C_1 = 3.74 \times 10^4$, $C_2 = 1.438 \times 10^4$, T is the internal temperature of said person at said point of infrared emissions where said temperature is detected, and $\lambda$ is a wavelength of said filter.

24. A method of noninvasively measuring a concentration of at least one predetermined constituent in a person's blood, comprising the steps of:

detecting infrared energy generated and emitted by the person in a wavelength range including n different wavelengths of at least 2.0 μm, said infrared energy containing energy at each of said n wavelengths which is differently absorbed by said at least one predetermined constituent whereby each predetermined constituent readily absorbs infrared energy at least one of said n wavelengths and minimally absorbs infrared energy at another of said n wavelengths, and outputting at least one detection signal representative of infrared energy at said n wavelengths which has been emitted by said person and selectively absorbed by said at least one predetermined constituent;

measuring an internal temperature of said person at a point where said infrared energy is detected in said detecting step;

determining the infrared emissions corresponding to said internal temperature measured in said temperature measuring step; and calculating the concentration of said at least one predetermined constituent as a function of the infrared energy detected in said detecting step and the determined infrared emissions determined in infrared emissions determining step.

25. A method as in claim 24, comprising the further step of synchronizing the detection of said infrared energy emitted by the person with systolic and diastolic phases of a cardiac cycle of the person.

26. A method as in claim 25, wherein said synchronizing step includes the step of determining diastolic and systolic time intervals respectively occurring during the systolic and diastolic phases of the cardiac cycle of the person, whereby said detecting step is performed during said systolic and diastolic time intervals.

27. A method as in claim 24, wherein said calculating step comprises the step of calculating the concentration C of said at least one predetermined constituent in accordance with the equation:

$$I/I_o = e^{-CLX},$$

where L is a pathlength from a point where said infrared energy is emitted to said point where said infrared energy is detected, X is an experimentally determined extinction coefficient, I is the infrared emissions detected in said infrared energy detecting step, and $I_o$ is the incident energy within said person at said point where said infrared energy is emitted, defined from Planck's equation as:

$$I_o = T_R * \epsilon * \frac{C_1}{\lambda^5 \left( e^{\frac{C_2}{\lambda T}} - 1 \right)}$$

where $T_R$ is a transmission coefficient of a filter which passes said at least one predetermined constituent, $\epsilon$ is emissivity of skin, $C_1=3.74\times10^4$, $C_2=1.438\times10^4$, T is the internal temperature of said person at said point where said infrared energy is emitted, and $\lambda$ is a wavelength of said filter.

28. A method as in claim 24, wherein said concentration calculating step includes the step of forming a ratio R=(Sys L1–Dias L1)/(Sys L2–Dias L2), where Sys L1 is a detected systolic phase signal at said one wavelength, Dias L1 is a detected diastolic phase signal at said one wavelength, Sys L2 is a detected systolic phase signal at said another wavelength, and Dias L2 is a detected diastolic phase signal at said another wavelength.

29. A method as in claim 28, wherein said concentration calculating step includes the steps of converting said ratio R from a voltage reading to a reading in watts and adding watts of infrared energy emitted by a chopper wheel of an infrared emissions detector to determine a temperature difference between said internal temperature and said chopper wheel, thereby eliminating discontinuities in said ratio R.

* * * * *

UNITED STATES PATENT AND TRADEMARK OFFICE
CERTIFICATE OF CORRECTION

PATENT NO. : 5,615,672
DATED : April 1, 1997
INVENTOR(S) : James R. Braig, Daniel S. Goldberger and Bernhard B. Sterling It is certified that error appears in the above-indentified patent and that said Letters Patent is hereby corrected as shown below:

Column 15, line 52, change "energy" to --emissions--.

Column 17, line 46, change "using" to --from--.

Column 18, Claim 24, line 26, change "at least" to --at at least--.

Signed and Sealed this

Twenty-eighth Day of October, 1997

Attest:

BRUCE LEHMAN

Attesting Officer

Commissioner of Patents and Trademarks